US009133434B1

(12) United States Patent
Cameron

(10) Patent No.: US 9,133,434 B1
(45) Date of Patent: Sep. 15, 2015

(54) GRASS ENDOPHYTE

(71) Applicant: Cropmark Seeds Ltd., Christchurch (NZ)

(72) Inventor: Nicholas Evan Cameron, Darfield (NZ)

(73) Assignee: Cropmark Seeds Ltd, Christchurch (NZ)

( * ) Notice: Subject to any disclaimer, the term of this patent is extended or adjusted under 35 U.S.C. 154(b) by 0 days.

(21) Appl. No.: 14/721,902

(22) Filed: May 26, 2015

Related U.S. Application Data

(62) Division of application No. 13/557,623, filed on Jul. 25, 2012.

(51) Int. Cl.
*C12N 1/00* (2006.01)
*A01N 65/00* (2009.01)
*A61K 36/06* (2006.01)
*A61K 36/09* (2006.01)
*A01H 15/00* (2006.01)
*A01H 5/00* (2006.01)

(52) U.S. Cl.
CPC . *C12N 1/00* (2013.01); *A01N 65/00* (2013.01)

(58) Field of Classification Search
None
See application file for complete search history.

(56) References Cited

U.S. PATENT DOCUMENTS

| 6,815,591 | B1 | 11/2004 | Hignight et al. |
| 7,976,857 | B2 | 7/2011 | Tapper et al. |
| 2008/0229441 | A1 | 9/2008 | Young et al. |
| 2011/0262401 | A1 | 10/2011 | Tapper et al. |

FOREIGN PATENT DOCUMENTS

| WO | WO 00/40075 | 7/2000 |

OTHER PUBLICATIONS

Blankenship et al. Phytochemistry 58 (2001), pp. 395-401.
Freeman et al., "Genetic Conversion of a Fungal Plant Pathogen to a Nonpathogenic, Endophytic Mutualist," Science, vol. 260, pp. 75-78 (Apr. 2, 1993).
Madigan et al., Biology of Microorganisms, 8th edition, Prentice Hall, Upper Saddle River Press, London, p. 309 (1997).
Schmid et al., "Ryegrass endophyte: host/fungus interaction," Grassland Research and Practice Series, No. 7, pp. 101-106 (1999).
Scott et al., "Functional analysis of the Epichloë festucae-perennial ryegrass symbiosis," Grassland Research and Practice Series, No. 13, A. Popay and E.R. Thom eds., NZ Grassland Assocn., pp. 433-441 (May 2007).
Simpson et al., "Spontaneous in planta changes in fungal endophytes impact symbiosis," Grassland Research and Practise Series, No. 13, A..Popay and E. Thom eds, NZ Grassland Assocn., pp. 191-193 (2007).

*Primary Examiner* — Chris R Tate
*Assistant Examiner* — Douglas F White
(74) *Attorney, Agent, or Firm* — Knobbe, Martens, Olson & Bear, LLP

(57) ABSTRACT

A method of protecting a host grass from stress, such as caused by insect pests, by artificially inoculating the host grass with an endophyte-containing composition is disclosed. The endophyte produces loline at a level sufficient to confer protection to the endophyte-infected host grass and does not produce detectable levels of alkaloids having toxicity to ruminant animals such as sheep, cattle, goats, or deer. In vitro cultures of the endophyte *Neotyphodium uncinatum*, var. U2 are disclosed as well as infected plants and seeds. The infected plants and seeds produce 5.0-20,000 μg lolines per gram dry weight of grass and do not produce detectable levels of alkaloids having toxicity to ruminant animals such as ergovaline, peramine, lolitrem B and epoxy-Janthitrems.

17 Claims, 2 Drawing Sheets

Photos of U2 endophyte colony

Photos of UNC1 endophyte colony

GRASS ENDOPHYTE

CROSS-REFERENCE TO RELATED APPLICATIONS

This application is a divisional of U.S. application Ser. No. 13/557,623, filed Jul. 25, 2012 which is incorporated herein by reference.

BACKGROUND OF THE INVENTION

1. Field of the Invention

This invention relates to fungal endophytes and combinations of endophytes with grass plants.

2. Description of the Related Art

Endophyte-infected grasses are relatively pest-resistant and drought-tolerant, making them ideal candidates for low maintenance situations such as turf purposes and erosion control. The endophyte does not affect either the growth or the appearance of the grass. Endophytes are transmitted only through seed and their presence requires a laboratory evaluation to confirm. Endophyte-infected grasses generally have low palatability to livestock and may lead to a variety of problems when used as livestock feed such as lameness, low energy, poor reproductive capacity both in conception and bringing the fetus to term, and low milk production. These problems are due to the presence of a range of alkaloids produced by the endophyte which are also responsible for the pest- and drought-resistance.

There is a need for an endophyte-infected grass plant that has low or non-detectable levels of certain alkaloids that may have deleterious effects on forage animals while still producing sufficient quantities of those alkaloids which provide a competitive advantage to the plant host. There is a need for endophyte-infected grasses that can be used as forage.

SUMMARY OF THE INVENTION

Embodiments of the invention are directed to an in vitro culture comprising *Neotyphodium uncinatum*, var. U2 and seeds from the family Poaceae that have been artificially infected with *Neotyphodium uncinatum*, var. U2. *Neotyphodium uncinatum*, var. U2 has been deposited with the Margot Forde Germplasm Centre, Ag Research Palmerston North, New Zealand as Accession No. V1746 on Feb. 4, 2014. Preferably, the seed is from a plant such as *Lolium perenne, Lolium hybridum, Lolium multiflorum, Festuca arundinacea, Festuca pratensis*, and *Festulohum* hybrids.

Embodiments of the invention are directed to isolated endophytes producing 5.0-20,000 µg lolines from infected grass/g dry plant material and not producing detectable levels of at least one alkaloid having toxicity to ruminant animals. In preferred embodiments, the alkaloid is ergovaline, peramine, lolitrem B or epoxy-Janthitrems. In preferred embodiments, the ruminant animals are sheep, cattle, goats, or deer. Preferably, the endophyte is *Neotyphodium uncinatum*, var. U2.

Embodiments of the invention are directed to plants of the family Poaceae artificially infected with *Neotyphodium uncinatum*, var. U2. In preferred embodiments, the plant is *Lolium perenne, Lolium hybridum, Lolium multiflorum, Festuca arundinacea, Festuca pratensis*, or *Festulohum* hybrids.

Embodiments of the invention are directed to methods of protecting a host grass from stress by artificially inoculating the host grass with an endophyte-containing composition to produce an endophyte-infected host grass. Preferably, the endophyte produces one or more lolines at a level sufficient to confer protection to the endophyte-infected host grass and does not produce detectable levels of one or more alkaloids having toxicity to ruminant animals. Preferably, the ruminant animals are sheep, cattle, goats, or deer.

In some embodiments, the stress is caused by an insect. Preferably, the insect is Argentine stem weevil (*Listronotus bonariensis*), New Zealand Grass Grub (*Costelytra zealandica*), Black beetle (*Heteronychus arator*), Porina (*Wiseana* sp.) or Red Headed Pasture cockchafer (*Adoryphorus couloni*).

In preferred embodiments of the method for protecting a host grass, the host grass is artificially inoculated with an endophyte-containing composition which includes *Neotyphodium uncinatum*, var. U2. Preferably, the endophyte produces 5.0-20,000 µg/g lolines (wt lolines/wt dry grass). Preferably, the grass is from the family Poaceae. More preferably, the grass is of the genus *Festuca*. In a most preferred embodiment, the grass is *Lolium perenne, Lolium hybridum, Lolium multiflorum, Festuca arundinacea, Festuca pratensis*, or *Festulohum* hybrids.

In preferred embodiments, levels of ergot alkaloids in the endophyte-infected host grass are less than detectable levels of 0.2 µg/g, (wt. alkaloid/dry wt. grass).

In preferred embodiments, levels of pyrrolopyrazine alkaloids in the endophyte-infected host grass are less than 0.1 µg/g, (wt. alkaloid/dry wt. grass).

In preferred embodiments, ergovaline, peramine, lolitrem B and epoxy-Janthitrems are not detectable in the endophyte-infected host grass.

DETAILED DESCRIPTION

Figure 1:
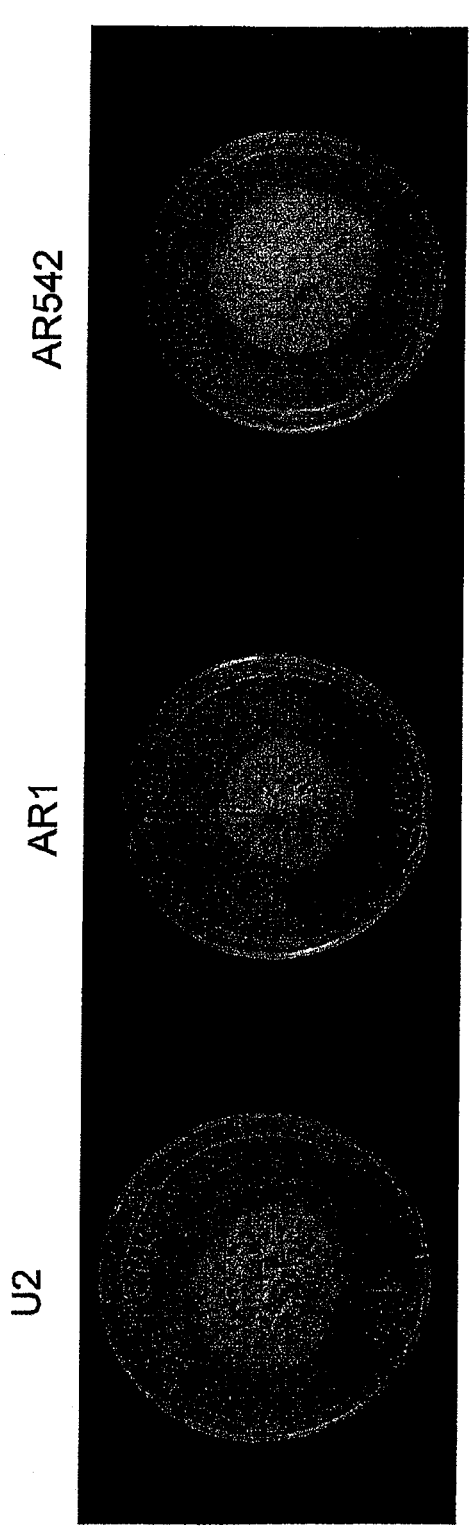
FIG. 1 shows a comparison of *Neotyphodium uncinatum*, var. U2 with AR542 (*N. coenophialum*) and AR1 (*N. lolii*) grown on agar.

Embodiments of the invention relate to *Neotyphodium uncinatum*, var. U2, common name, Fungal Endophyte, Meadow Fescue. The endophyte was identified in line FP102 of *Festuca pratensis* after screening many *Festuca* lines. The FP102 line originally came from Norway in 1999. The endophyte was isolated in New Zealand. The native host for this endophyte is the plant and seed of *Festuca pratensis*. As with all endophytes, *Neotyphodium uncinatum*, var. U2 is naturally reproduced by vertical transmission, growing into the seed of the host. The ability to sexually reproduce (sporulate) or transmit horizontally in nature has been lost.

In some embodiments an isolated endophyte *Neotyphodium uncinatum*, var. U2, is provided. The isolated endophyte may be in an in vitro culture. Plants such as grass can be infected with the isolated endophyte. Thus, in some embodiments grass artificially infected with *Neotyphodium uncinatum*, var. U2 is provided. In some embodiments, seed artificially infected with *Neotyphodium uncinatum*, var. U2 or obtained from grass artificially infected with *Neotyphodium uncinatum*, var. U2 is provided. When a grass plant is artificially inoculated with *Neotyphodium uncinatum*, var. U2, the infected plant produces loline alkaloids which provide a competitive advantage to the infected plant, but the infected grass plant does not produce levels of alkaloids that are deleterious to forage animals.

Infection of the grass with *Neotyphodium uncinatum*, var. U2 confers one or more advantages to the grass relative to uninfected control plants. These advantages include protection from pests relative to uninfected control plants, including but not limited to insects and nematodes and/or resistance to stress such as spatial competition from other plant species, water or nutrient deficiency, stress due to heat or cold and the like. In some embodiments, advantages include greater vigour such as more roots, higher total biomass, more tillers and/or higher seed production relative to uninfected control plants. In some embodiments, the advantage includes protection from disease, relative to uninfected control plants.

Embodiments of the invention are directed to methods of producing grass plants artificially infected with *Neotyphodium uncinatum*, var. U2 which have some competitive advantage relative to uninfected plants, but are not toxic to ruminants.

In some embodiments, the competitive advantage includes protecting the plant from stress. The stress may be biotic or abiotic. The stress may be biotic and caused by an animal pest, such as an insect or nematode. In some embodiments, stress may be abiotic such as water or nutrient deficiency, temperature stress, or spatial competition from other species. The stress may be a combination of biotic and abiotic stress.

In some embodiments, the competitive advantage may include improved vigor compared to plants which are not infected with *Neotyphodium uncinatum*, var. U2. Grass plants infected with *Neotyphodium uncinatum*, var. U2 according to embodiments of the invention may have more root growth, more tillers, more total biomass and/or more seed production than the corresponding grass plants which are not infected with *Neotyphodium uncinatum*, var. U2.

In some embodiments, the competitive advantage may include disease resistance.

*Neotyphodium uncinatum*, var. U2 may be propagated by in vitro propagation including but not limited to inoculation of seedlings. *Neotyphodium uncinatum*, var. U2 may be maintained in seed and/or in vitro culture (isolated from the plant host on agar). In some embodiments, *Neotyphodium uncinatum*, var. U2 may be reproduced by vegetative propagation, paralleling the life cycle of the host plant. *Neotyphodium uncinatum*, var. U2, although native to *F. pratensis*, can be successfully inserted artificially into other grass species including but not limited to *Lolium perenne, Lolium hybridum, Lolium multiflorum, Festuca arundinacea, Festuca pratensis*, and *Festulohum* hybrids by known methods. In a preferred embodiment, seedling inoculation is performed using endophyte grown rapidly over 10 to 14 days, for example in a liquid potato dextrose broth which is then filtered to remove excess broth. Inoculation may be performed by inserting this prepared endophyte into a slit incision in the meristem area of a seedling plant grown for 7 to 10 days from endophyte free seed under zero light and 15-25° C., preferably about 20° C. conditions. Slit incision is carried out using a syringe needle, such as a 30 gauge syringe needle. After the endophyte is inoculated into the slit incision, the plants are placed back in dark conditions for a further 7 to 10 days before being adapted to low light conditions for 3-4 days and eventually planted into a fine potting mix. Plants are checked for endophyte presence when they reach the 3-5 tiller stage and checked for the presence of the correct endophyte strain using DNA markers.

When the host is infected with *Neotyphodium uncinatum*, var. U2, the production of loline metabolites (N-formyl loline, N-acetyl loline, N-acetyl norloline, N-methyl loline, for example) by the endophyte act as a feeding deterrent to many pasture pests. However, lolines are not known to be toxic to grazing animals such as sheep, cattle, goats, and deer.

In some embodiments, one or more of the recited loline metabolites are at elevated levels relative to control plants that are not infected with var. U2.

Grasses infected with *Neotyphodium uncinatum*, var. U2 show resistance to insect pests including but not limited to Argentine stem weevil (*Listronotus bonariensis*), New Zealand Grass Grub (*Costelytra zealandica*), Black beetle (*Heteronychus arator*), Porina (*Wiseana* sp.) and Red Headed Pasture cockchafer (*Adoryphorus coulonii*).

Grasses infected with *Neotyphodium uncinatum*, var. U2 have reduced root consumption by root feeding larvae of grass grub, black beetle and cockchafer, less leaf shredding by Argentine stem weevil, and less consumption by porina larvae and adult black beetle and as a consequence, greater vigour and production. Grasses infected with *Neotyphodium uncinatum*, var. U2 show no visibly detectable difference with uninfected grasses of the same species.

As mentioned above, grasses infected with *Neotyphodium uncinatum*, var. U2 produce lolines which are alkaloids which have been shown to be either toxic or a feeding deterrent to a range of pest insects including those listed above. Loline alkaloids are a group of compounds with distinct chemical and biological features. Chemically, lolines are characterized by a saturated pyrrolizidine ring, a primary amine at the C1 carbon and an internal ether bridge joining distant ring members C2 and C7. This internal ether bridge is uncommon among organic compounds and is a characteristic feature of lolines. Different substituents at the C1 carbon provide different bioactivity against insects. Such substituents include methyl, formyl and acetyl groups.

The biological activity attributed to lolines includes resistance to herbivores, drought resistance and spatial competition. In preferred embodiments of the invention, lolines are present at concentrations sufficient to confer protection to the host grass against at least one insect pest. For example total loline concentrations of greater than 400 µg/g deter New Zealand grass grub from feeding and concentrations greater than 1000 µg/g reduce shredding by Argentine stem weevil. In preferred embodiments, the pest is selected from insect species from the orders of Homoptera, Hemiptera, Coleoptera, Hymenoptera, Lepidoptera, and Blattaria. More preferably, the insect pest is selected from Argentine stem weevil (*Listronotus bonariensis*), New Zealand Grass Grub (*Costelytra zealandica*), Black beetle (*Heteronychus arator*), Porina (*Wiseana* sp.) and Red Headed cockchafer (*Adoryphorus couloni*). The characteristics of the resistance may include killing of insects feeding on the endophyte-infected grass, avoidance of the endophyte-infected grass by insect pests, effects on fecundity of insect pests such as reduced or no production of offspring or impaired insect development. In preferred embodiments, insect pests are repelled and as a consequence, development is arrested due to malnutrition. In some embodiments, pests or their larvae, particularly Porina larvae, are killed by exposure to lolines.

In preferred embodiments, the level of total lolines produced by the endophyte is 1.0 µg/g to 20,000 µg/g, (wt. loline/dry wt. grass), more preferably at levels in excess of 400 µg/g, yet more preferably at levels in excess of 1,000 µg/g, yet more preferably at levels in excess of 5,000 µg/g in above ground plant parts. In a preferred embodiment, total loline measurement is performed using gas chromatography (GC-FID). The following protocol is exemplary. Freeze dried finely ground plant material (about 0.25 g) is added to 5 ml of solvent (95:5 dichloromethane:ethanol) in an 8 ml glass vial. This solvent contains phenylmorpholine (6 mg/100 ml) as an internal standard. Then 250 µl of saturated sodium bicarbonate solution (2 g/10 ml) is added to the vial. The vials are shaken on an orbital shaker for 1 hour. The vial is left to settle and the supernatant filtered using a plugged Pasteur pipette into a clean vial. 1 ml of this extract is then transferred to a GC vial for analysis.

In a preferred embodiment, samples are analyzed using a gas chromatograph (GC) (Shimadzu 2010) equipped with a flame ionization detector (FID). The column is a ZB 624 of 30 m, 0.25 mm I.D. and a film of 1.40 µm. The film is 6% cyanopropylphenyl and 94% dimethylpolysiloxane. The oven is set at an initial temperature of 90° C., held for 1 min, then increased (ramped) to 260° C. at 30° C./min, and held for 10 min. Injector temperature is 250° C. Gas flow is a constant flow of 1.2 ml/min. The retention times of N-Methyl Loline, N-Formyl Loline, N-Acetyl Loline, and N-Acetyl Nor Loline are determined as 8.0, 13.2, 13.7, and 12.2 minutes respectively. Total loline concentration is the sum of the four loline compounds assessed above. The limit of detection of loline alkaloids is considered to be 5 µg/g. Other known protocols for measuring levels of loline alkaloids could also be used.

In preferred embodiments, the grass infected with *Neotyphodium uncinatum*, var. U2 does not produce detectable levels of ergot alkaloids, such as ergovaline. As ergot alkaloids are more closely associated with toxicity to ruminants, in preferred embodiments, grasses infected with *Neotyphodium uncinatum*, var. U2 are not toxic to ruminants. For example, in preferred embodiments, total levels of ergot alkaloids in the endophyte-infected host grass are less than 5 µg/g, more preferably less than 1 µg/g and yet more preferably below detectable levels of 0.2 µg/g, (wt. alkaloid/dry wt. grass).

In preferred embodiments, the grass infected with *Neotyphodium uncinatum*, var. U2 does not produce detectable levels of senecio-type alkaloids. Such alkaloids are associated with liver damage. Accordingly, grasses infected with *Neotyphodium uncinatum*, var. U2 do not produce detectable liver damage in ruminants feeding upon the grasses. Limit of detection of loline alkaloids are considered to be 5 µg/g.

In preferred embodiments, total levels of pyrrolopyrazine alkaloids, such as peramine, in the endophyte-infected host grass are less than 2.0 µg/g, more preferably less than 1.0 µg/g yet more preferably, less than 0.1 µg/g, (wt. alkaloid/dry wt. grass). 0.1 µg/g (wt alkaloid/dry wt. grass) are at the detection limit. Levels below 0.1 µg/g are considered non-detectable.

Other alkaloids produced by endophytes include lolitrem B and epoxy-janthitrems. In preferred embodiments, host grasses infected with *Neotyphodium uncinatum*, var. U2 contain low or non-detectable levels of these alkaloids. "Non-detectable" with respect to these other alkaloids means that these alkaloids are not detectable using the current protocols used to measure them.

Ruminant livestock that can be fed grasses infected with *Neotyphodium uncinatum*, var. U2 include but are not limited to sheep, cattle, goats, and deer. These ruminant animals can feed on grasses infected with *Neotyphodium uncinatum*, var. U2 in either a commercial setting such as a farm or ranch or in the wild. Such commercial settings include raising livestock for meat, dairy products, and textile production such as wool, mohair and leather and include systems where livestock are enclosed in pastures or barns or not enclosed or allowed to range freely but with some limited enclosure.

*Neotyphodium uncinatum*, var. U2 is stable, uniform and clearly distinguishable from any other variety of endophyte. This variety was isolated in New Zealand from line FP102 of *Festuca pratensis* from Norway. A PVR has been granted in New Zealand as FEN009.

Grasses infected with *Neotyphodium uncinatum*, var. U2 are useful in a variety of settings including but not limited to turf, forage, as ornamentals and for erosion control. Such grasses include species of the family Poaceae, preferably of the genera *Festuca* and *Lolium*, more preferably of the species *Lolium perenne, Lolium hybridum, Lolium multiflorum, Festuca arundinacea, Festuca pratensis,* and *Festulohum* hybrids.

In some embodiments, a commercial variety of grass is infected with *Neotyphodium uncinatum*, var. U2 using the technique described above using meristem slit inoculation or by recurrent pair-crossing using the meadow fescue host and continuous top-crossing over repeated cycles to the desired parent. This infected grass is used to provide forage for ruminant animals or for turf or usage as a break crop to remove certain insect or nematode pests. The grass shows resistance to a range of insect and nematode pests and is hardier than the same commercial grass not infected with *Neotyphodium uncinatum*, var. U2. Ruminant animals feeding on the *Neotyphodium uncinatum*, var. U2-infected grass were similar to animals fed on non-infected grass of the same commercial variety. This can be measured in various ways known to those in the art including weight gain of the animal and animal milk production. In preferred embodiments, ruminant animals feeding on the *Neotyphodium uncinatum*, var. U2-infected grass were similar in weight gain to animals fed on non-infected grass of the same commercial variety.

Example 1

Isolation of *Neotyphodium uncinatum*, Var. U2 and Comparison with Similar Strains

*Neotyphodium uncinatum*, var. U2 was isolated from line FP102 of *Festuca pratensis* (Meadow fescue). Line FP102 originally came from Norway in 1999. Characteristics for *Neotyphodium uncinatum*, var. U2 were determined and compared with other varieties. For these tests, the endophytic fungus isolated was cultured on 1.5% (w/v) potato dextrose agar at 20° C. in the dark (Christensen M J, Latch G C M, Tapper S A 1991: Variation within isolates of *Acremonium* endophytes from perennial ryegrasses. Mycol. Res. 95: 918-923). Length of cultivation was generally standardized at 4 weeks, but may be varied according to the isolate. Five plates of each strain were grown.

1) Colony: Rate of Growth

Colony radial diameter was measured (two diameters, at right angles, per plate) after 1 week's growth and again after 2, 3 and 4 weeks growth. Radial growth rate per day was calculated and rated "very slow", "slow", "medium", "rapid" or "very rapid".

2) Colony: Sporulation

Colonies were examined under a stereo/dissecting microscope after 4 weeks. Confirmation of sporulation was through preparing slides (mounting in lactophenol, plus or minus cotton blue stain) and examining under compound microscope at approximately 400× magnification or 1000× (as appropriate). Sporulation was rated as "absent" or "present".

3) Colony: Sectoring

Each of the 5 duplicate plates from 1) above were examined after 4 weeks of growth and sectoring noted as "absent" or "present".

4) Colony: Colour (Upper Surface)

Each of the 5 duplicate plates from 1) above were examined after 4 weeks of growth and color noted as "white" or "brown".

5) Colony: Shape

Each of the 5 duplicate plates from 1) above was examined after 4 weeks of growth and the colony shape determined and noted as "flat", "raised", "brainlike", "smooth", "convolute" or "domed".

6) Colony: Texture

Each of the 5 duplicate plates from 1) above was examined after 4 weeks of growth and texture noted as "waxy" or "dry".

7) Colony: Immersion of Margin in Agar

Each of the 5 duplicate plates from 1) above was examined after 4 weeks of growth and colony margin noted as "immersed" or "superficial".

8) Colony: Resistance to Benomyl on Growth

Plates of PDA containing different concentrations of the fungicide benomyl were prepared as outlined by Christensen et al. (1991). Benlate(Methyl[1-[(butylamino)carbonyl]-1H-benzimidazol-2-yl]carbamate) (50% WP) was added to PDA prior to sterilization. Concentrations of benomyl were adjusted to 1, 5, 10, 50 and 100 ppm. Five duplicate plates were inoculated with a colony plug. The concentration at which growth does not occur indicative of resistance was recorded after 4 weeks as "absent or very weak", "weak", "medium", "strong" or "very strong".

9) Aerial Mycelium: Density

Each of the 5 duplicate plates from 1) above was examined after 4 weeks of growth and amount of aerial mycelium noted as "very sparse", "sparse", "medium", "dense" or "very dense".

10) Aerial Mycelium: Type

Each of the 5 duplicate plates from 1) above was examined after 4 weeks of growth and the aerial mycelium determined as "felted", "cottony" or "tufted erect".

11) Conidia: Length 25 conidia (from at least 2 duplicate plates) were measured using a 40× microscope objective and a ColorView imaging analysis system. The spore range, mean, and a descriptive term (very short, short, medium, long or very long) was given. ("medium" is 5-7 µm.)

12) Conidia: Width 25 conidia (from at least 2 duplicate plates) were measured using a 40× microscope objective and a ColorView imaging analysis system. The spore range, mean, and a descriptive term (very narrow, narrow, medium, broad or very broad) was given. ("medium" is 2-4 µm.)

TABLE 1

Characteristics of *Neotyphodium uncinatum*, var. U2

| Characteristics | State of Expression |
| --- | --- |
| Colony: shape | convoluted |
| Colony: growth rate | medium (0.15 mm-0.3 mm per day) |
| Colony: sectoring | absent |
| Colony: color (upper surface) | white |
| Colony: texture | dry |
| Colony: immersion of margin in agar | Superficial (sits on top) |
| Colony: resistance to benomyl on growth | strong |
| Aerial mycelium: density | medium |
| Aerial mycelium: type | felted |
| Sporulation: in culture | absent |
| Metabolite: loline | present |
| Metabolite: ergovaline | absent |
| Metabolite: peramine | absent |
| Metabolite: lolitrem B | absent |
| Metabolite: epoxy-Janthitrem | absent |

TABLE 2

Comparison of *Neotyphodium uncinatum*, var. U2 to similar varieties

| Denomination of similar variety | Characteristic in which the similar variety is different | State of expression of similar variety | State of expression of *Neotyphodium uncinatum*, var. U2 |
| --- | --- | --- | --- |
| AR1 (*N. lolii*) | Colony: shape | brain like | convoluted |
| | Metabolite: peramine | present | absent |
| | Metabolite: loline | absent | present |
| AR542 | Sporulation: in culture | present | absent |
| (*N. coenophialum*) | Colony: shape | raised | convoluted |
| | Metabolite: peramine | present | absent |
| NEA2 | Metabolite: ergovaline | present | absent |
| (*N. lolii*) | Metabolite: peramine | present | absent |

A comparison of *Neotyphodium uncinatum*, var. U2 with AR542 (*N. coenophialum*) and AR1 (*N. lolii*) grown on agar is shown in FIG. 1.

Example 2

Comparison of *Neotyphodium uncinatum*, Var. U2 with Variety *Neotyphodium uncinatum*, Var.UNC1

Figure 2:
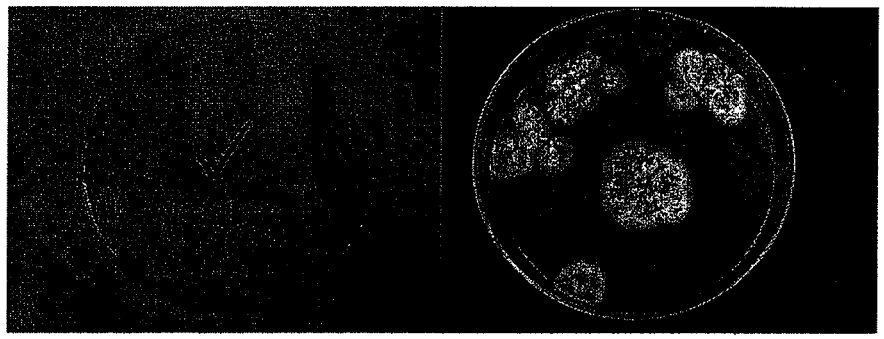
FIG. 2 shows a comparison between endophyte colonies of *Neotyphodium uncinatum*, var.U2 and variety UNC1.
Figure 2:
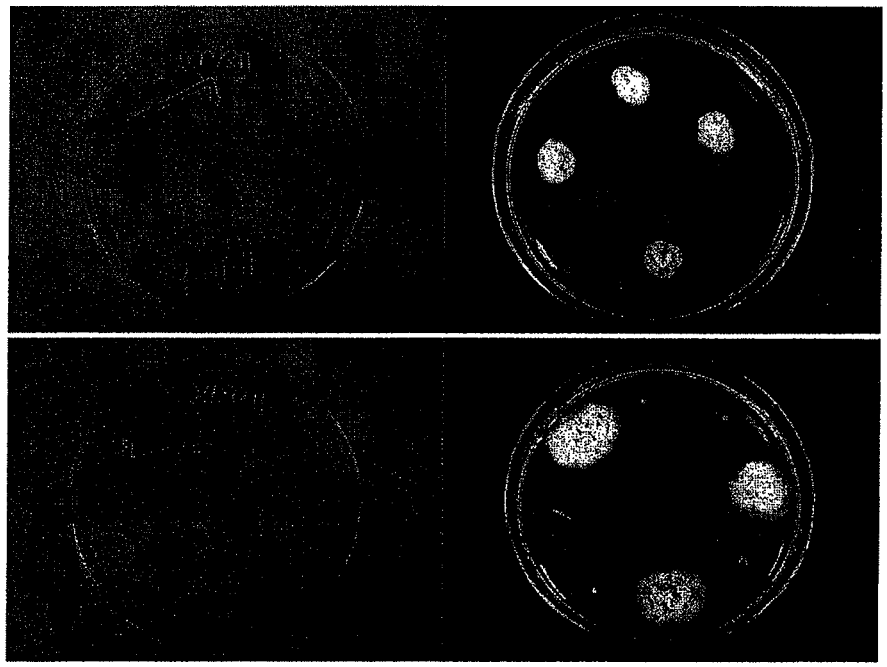

The two varieties were similar in tested characteristics of colony sporulation, colony sectoring, colony color (upper surface), colony shape, colony immersion or margin in agar, colony texture, aerial mycelium density and type, and effect of benomyl on growth. The two varieties differed in colony shape and rate of growth. *Neotyphodium uncinatum*, var.UNC1 showed a strong growth rate while *Neotyphodium uncinatum*, var.U2 showed a medium growth rate. Colony shape differed as shown in FIG. 2.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of protecting a host grass from stress, comprising artificially inoculating the host grass with an effective amount of an endophyte-containing composition comprising an in vitro culture comprising *Neotyphodium uncinatum*, var. U2 to produce an endophyte-infected host grass, wherein the endophyte produces lolines at a level sufficient to confer protection to the endophyte-infected host grass and does not produce detectable levels of alkaloids having toxicity to ruminant animals.

2. The method of claim 1, wherein the stress is caused by an insect.

3. The method of claim 2, wherein the insect is selected from the group consisting of Argentine stem weevil (*Listronotus bonariensis*), New Zealand Grass Grub (*Costelytra zealandica*), Black beetle (*Heteronychus arator*), Porina (*Wiseana* sp.) and Red Headed Pasture cockchafer (*Adoryphorus couloni*).

4. The method of claim 1, wherein the endophyte produces 5.0-20,000 µg/g (wt lolines/wt dry grass).

5. The method of claim 1, wherein the grass is from the family Poaceae.

6. The method of claim 5, wherein the grass is selected from the group consisting of the genus *Festuca*.

7. The method of claim 5, wherein the grass is selected from the group consisting of *Lolium perenne, Lolium hybri-

*dum, Lolium multiflorum, Festuca arundinacea, Festuca pratensis*, and *Festulolium* hybrids.

8. The method of claim 1, wherein levels of ergot alkaloids in the endophyte-infected host grass are less than detectable levels of 0.2 µg/g, (wt. alkaloid/dry wt. grass).

9. The method of claim 1, wherein levels of pyrrolopyrazine alkaloids in the endophyte-infected host grass are less than 0.1 µg/g, (wt. alkaloid/dry wt. grass).

10. The method of claim 1, wherein ergovaline, peramine, lolitrem B and epoxy-Janthitrems are not detectable in the endophyte-infected host grass.

11. The method of claim 1, wherein the ruminant animals are sheep, cattle, goats, or deer.

12. The method of claim 1, wherein a seedling of the host grass is artificially inoculated with an effective amount of the endophyte-containing composition.

13. The method of claim 12, wherein the seedling inoculation comprises inserting the endophyte-containing composition into a slit incision in the meristem of the seedling.

14. The method of claim 13, wherein the seedling is grown for 7-10 days from endophyte-free seed prior to inoculation.

15. The method of claim 13, wherein the inoculated seedlings are grown for 7 to 10 days in dark conditions after inoculation.

16. The method of claim 13, wherein plants produced from the seedlings are checked for presence of *Neotyphodium uncinatum*, var. U2 using DNA markers.

17. The method of claim 13, wherein preparation of the endophyte-containing composition comprises growth in liquid potato dextrose broth.

\* \* \* \* \*

UNITED STATES PATENT AND TRADEMARK OFFICE
CERTIFICATE OF CORRECTION

PATENT NO. : 9,133,434 B1
APPLICATION NO. : 14/721902
DATED : September 15, 2015
INVENTOR(S) : Nicholas Evan Cameron Page 1 of 1

It is certified that error appears in the above-identified patent and that said Letters Patent is hereby corrected as shown below:

In the Specification

In column 1 at line 48, Change "Festulohum" to --Festulolium--.

In column 1 at line 61, Change "Festulohum" to --Festulolium--.

In column 2 at lines 18-19 (approx.), Change "Festulohum" to --Festulolium--.

In column 3 at line 45, Change "Festulohum" to --Festulolium--.

In column 6 at line 5 (approx.), Change "Festulohum" to --Festulolium--.

Signed and Sealed this
Third Day of May, 2016

Michelle K. Lee
*Director of the United States Patent and Trademark Office*